(12) United States Patent
Fox et al.

(10) Patent No.: US 7,244,857 B2
(45) Date of Patent: Jul. 17, 2007

(54) METHOD OF MAKING HYDROXYALKYL AMIDE CONTAINING REDUCED LEVEL OF UNREACTED ALKANOLAMINE

(75) Inventors: E. Brian Fox, Monroe, CT (US); Timothy L. Lambert, Waterbury, CT (US)

(73) Assignee: Crompton Corporation, Middlebury, CT (US)

( * ) Notice: Subject to any disclaimer, the term of this patent is extended or adjusted under 35 U.S.C. 154(b) by 150 days.

(21) Appl. No.: 10/713,805

(22) Filed: Nov. 14, 2003

(65) Prior Publication Data

US 2005/0107623 A1    May 19, 2005

(51) Int. Cl.
  *C07C 231/00*    (2006.01)
(52) U.S. Cl. .................................................... 554/69
(58) Field of Classification Search .................. 554/69
  See application file for complete search history.

(56) References Cited

U.S. PATENT DOCUMENTS

| 4,208,293 A | 6/1980 | Zaweski |
| 4,729,769 A | 3/1988 | Schlicht et al. |
| 4,960,530 A | 10/1990 | Everett et al. |
| 5,154,844 A | 10/1992 | Perozzi |
| 5,164,102 A | 11/1992 | Everett et al. |
| 6,524,353 B2 | 2/2003 | de Rosa et al. |
| 6,531,571 B1 | 3/2003 | Gray |

FOREIGN PATENT DOCUMENTS

| WO | 92/06070 | * | 4/1992 |
| WO | WO 92/06070 | | 4/1992 |

* cited by examiner

*Primary Examiner*—Deborah D Carr
(74) *Attorney, Agent, or Firm*—Michael P. Dilworth

(57) ABSTRACT

A method for reacting alkanolamine with ester in the presence of a metal silicate compound and, optionally, a catalyst, to produce a hydroxyalkyl amide composition with a decreased level of alkanolamine and residual catalyst.

65 Claims, No Drawings

METHOD OF MAKING HYDROXYALKYL AMIDE CONTAINING REDUCED LEVEL OF UNREACTED ALKANOLAMINE

BACKGROUND OF THE INVENTION

1. Field of the Invention

This invention relates to a method for producing a fuel or lubricant additive composition that contains a decreased level of reactant components.

2. Description of Related Art

Fuel economy standards mandated by the federal government have resulted in efforts by the automotive industry to improve the fuel economy of motor vehicles. One way to reduce fuel consumption is by reducing friction in particular areas of the engine, e.g., bearings, valve trains, pistons, rings, water and oil pumps. A moderate decrease in the friction of these components will be reflected in a corresponding fuel economy improvement. Therefore, there has been an ongoing search for friction modifier compositions that will decrease friction in these key areas and thus improve fuel economy.

Various types of additives have been used as friction modifiers. Some of the more commercially and conventionally used friction modifiers are fatty acid esters, fatty acid amides and fatty acid ester-amides. U.S. Pat. No. 4,960,530 discloses an example of a lubricant additive and composition that can reduce friction.

Hydroxyalkyl amides have been used extensively as friction modifiers. U.S. Pat. No. 4,729,769 discloses a fatty acid amide detergency additive which is the reaction product of a $C_6$–$C_{20}$ fatty acid ester and a mono- or di-(hydroxy hydrocarbonyl) amine.

U.S. Pat. No. 4,208,293 discloses a lubricating oil adapted for use as a crankcase lubricant in internal combustion engines containing a friction-reducing amount of a fatty acid amide or ester of diethanolamine.

Although the production of hydroxyalkyl amides as friction modifiers for fuel and lubricant additives amongst other things has been quite extensive, most of processes for producing hydroxyalkyl amides produce a composition that retains a certain percentage of unreacted alkanolamine, together with other undesirable residuals. Certain end-use users desire hydroxyalkyl amides as friction modifying fuel and lubricant additives with a decreased level and/or a zero level of alkanolamine and/or residual catalyst. Therefore, it would be advantageous to provide a process for producing hydroxyalkyl amides with a low level or a zero level of alkanolamine and/or residual catalyst.

SUMMARY OF THE INVENTION

It is an object of the invention to provide a method of making hydroxyalkyl amide composition with a decreased level of alkanolamine.

It is a further object of the invention to provide a method of making a hydroxyalkyl amide composition with a decreased level of residual catalyst.

It is still further an object of the invention to provide a method of making a liquid engine fuel or lubricant composition containing a friction-modifying or lubricity amount of hydroxyalkyl amide composition that possesses a decreased level of residual alkanolamine and/or residual catalyst.

In keeping with these and the other objects of the invention, there is provided a method for reacting at least one primary and/or secondary alkanolamine with at least one ester or fatty natural materials, optionally, in the presence of catalyst, to provide a reaction mixture containing hydroxyalkyl amide and unreacted alkanolamine, wherein the improvement comprises, carrying out the reaction of alkanolamine and ester in the presence of at least one metal silicate or treating the reaction mixture with at least one metal silicate, the metal of the metal silicate being a metal of Group IA, Group IIA or Group IIIA of The Periodic Table.

Furthermore, in accordance with the invention, there is provided a method of making a liquid engine fuel composition or lubricant comprising a major amount of liquid hydrocarbon fuel or lubricant and a minor amount of a hydroxyalkyl amide composition containing hydroxyalkyl amide obtained from primary and/or secondary alkanolamine, metal silicate and ester, the hydroxyalkyl amide containing less than 0.5 wt. percent of alkanolamine.

DETAILED DESCRIPTION OF THE INVENTION

The primary and/or secondary alkanolamine of the current invention has the general formula RNHR' wherein R is hydroxyalkyl of from 2 to about 10 carbon atoms, or hydroxyalkylether and/or combinations thereof, and R' is hydrogen, alkyl of from 1 to about 10 carbon, hydroxyalkyl of from 2 to about 10 carbon atoms, hydroxyalkylether and/or combinations thereof. Preferably, the alkanolamine will be a dialkanol amine, or dialkanolamine ether, most preferably diethanol amine, although other primary and secondary alkanolamines can be used. Mixtures of various primary and secondary alkanolamines can be utilized as well. Examples of primary and secondary alkanolamines are ethanolamine, propanolamine, isopropanolamine, butanolamine, isobutanolamine, methylethanolamine, butylethanolamine, diethanolamine, dipropanolamine, diisopropanolamine, dibutanolamine, diisobutanolamine, and mixtures thereof. In addition, alkanol amine groups reacted with alkoxides can be used. Examples of alkoxides are propylene oxide, ethylene oxide, and butylene oxide.

The amount of primary and/or secondary alkanol amine will be dependent on the desired hydroxyalkyl amide, but generally the molar ratio of primary and/or secondary alkanolamine to ester will be preferably from about 0.75:1 to about 1.25:1, more preferably from about 0.90:1 to about 1.10:1, and most preferably from about 0.95:1 to about 1.05:1.

The parent acid of the ester can be a fatty acid derived from natural materials such as canola oil, castor oil, cocoa butter, coconut oil, cotton seed oil, olive oil, palm kernel oil, palm kernel (olein), palm kernel (stearine), peanut oil, rapeseed oil, safflower oil, soybean oil, sunflower oil, tall oil, corn oil, butter, lard, tallow, yellow grease, blubber, herring, menhaden, sardine oil, babasso oil and mixtures thereof. Preferably, the ester will be a fatty acid methyl ester or mixture of fatty acid methyl esters, preferably, the parent acid of the ester is a fatty acid derived from coconut oil and the parent alkanol of the ester is methanol, although any methyl ester of the above-described natural materials can be used. In addition, instead of, or in combination with the ester and alkanolamine, a fatty acid can be used. Examples of fatty acids that can be used alone or in combination with ester are the same or different fatty acids that are the parent acid of the ester. If a fatty acid is used alone or in combination with the ester and alkanolamine, the reaction products then can be fatty acid amide as well as water. The process of the current invention is preferably conducted in the absence of water to prevent unwanted side reactions such as the hydrolysis of the ester and amide to acid and alcohol or amine. In addition, instead of, or in combination with the ester and alkanolamine, the fatty natural materials themselves can be used. Examples of fatty natural materials that can be used alone or in combination with ester are the same as the sources for the parent acid of the esters listed above. If a fatty natural material is used alone or in combination with the ester and alkanolamine, the reaction products then can be fatty acid amide as well as glycerin. The process of the current invention is preferably conducted without glycerin. The parent acid of the ester contains from about 4 to about 22 carbon atoms and the parent alkanol of the ester contains from 1 to about 10 carbon atoms.

Fatty acid esters are known to encompass esterified carboxylic acids such as monoglycerides, diglycerides and triglycerides, as well as straight chain carboxylic acids that have been esterified. Polymeric fatty acid esters are also contemplated as fatty acid esters. Examples of polymeric fatty acid esters are ester based on dimer and trimer acids like Arizona Chemicals Century 1156, Undyme 14 or Unidyne 60 and Uniqema's Pripol 1017 or 1006 and similar type materials. Various combinations and mixtures of the above-described natural matter can be used.

The amount of ester will be present in a molar ratio of alkanolamine to ester as described above.

The parent acid of the ester used in the current invention is generally made from a fatty acid. The fatty acid used to make the fatty acid ester and preferably the fatty acid methyl ester can vary depending on the desired fatty acid ester but can include acids such as, butyric, caproic, caprylic, capric, decenoic, lauric, cis-9-dodecenoic, myristic, myristoleic, cis-9-tetradecenoic, pentadecanoic, palmitic, palmitoleic, cis-9-hexadecenoic, heptadecanoic, heptadecenoic, steric, oleic, linoleic, linolenic, ricinoleic, dihydroxystearic, nonadecanoic, arachidic, cis-9, cis-11-eicosenoic, eicosadienoic, eicosatrienoic, arachidonic, eicosapentaenoic, behenic, erucic, docosadienoic, 4,8,12,15,19-docosapentaenoic, docosahexaenoic, lignoceric, tetracosenoic and mixtures thereof.

The alkanolamine and ester can be reacted optionally in the presence of catalyst. The catalyst can be present either in concentrate or in solvent. Suitable solvents for the catalyst can include any volatile alcohol containing up to about six carbon atoms such as methanol, ethanol, isopropanol, n-propanol, butanol, t-butanol and sec-butanol, normal or branched pentanols, normal or branched hexanols. If a solvent is used, it can be present in any amount necessary to solvate the catalyst, which is preferably a solution of from about 1 to about 100, more preferably from about 10 to about 50 and most preferably from about 20 to about 30 wt. percent of catalyst concentrate in solvent. Generally, a basic catalyst will be used, such as an alkoxide or carbonate catalyst, preferably a metal alkoxide catalyst. Examples of suitable metal alkoxide and carbonate catalysts can include sodium methoxide, sodium ethoxide, sodium propoxide, potassium methoxide, potassium ethoxide, potassium propoxide, sodium or potassium butoxide, sodium or potassium pentoxide, sodium or potassium hexanoate, sodium carbonate, potassium carbonate, cesium carbonate, calcium carbonate, strontium carbonate, barium carbonate and mixtures thereof, with sodium methoxide being most preferred. The amount of metal alkoxide or carbonate catalyst will be in a catalytically effective amount which can vary greatly but will preferably be from about 0.05 to about 1.00, more preferably from about 0.25 to about 0.75 and most preferably from about 0.40 to about 0.60 wt. percent. In addition, organic catalysts such as tetraalkyl ammonium hydroxide can be used as well as Ethyl di-isopropyl amines, Hunig's Base (diisopropylethyl amine), DBU(1,8-diazabicyclo [5.4.0] undec-7-ene), DBN (1,5-diazabicyclo[4.3.0] non-5-ene), guanidine, Penta methyl guanadine. The amount of organic catalyst can vary greatly but will preferably be from about 0.05 to about 1.00, more preferably from about 0.25 to about 0.75, and most preferably from about 0.40 to about 0.60 wt. percent.

The current invention employs the above-described reactants for producing a hydroxyalkyl amide composition in the presence of at least one metal silicate or treats the hydroxyalkyl amide composition produced by the above-described reactants with metal silicate. Metal silicates are known sodium scavengers and have been commercially used to lower the sodium level in various chemical products. Suitable examples of the metal silicates include any metal silicate wherein the metal is from Group IA, Group IIA or Group IIIA of The Periodic Table. Examples of preferable metals include magnesium, calcium, aluminum and sodium with magnesium being the most preferable metal. Suitable metal silicates are of the general formula $xM_aO_b:ySiO_2:zH_2O$ wherein, as described above, M is any Group IA, Group IIA or Group IIIA metal, x and y are in a molar ratio of from about 1.5:1 to about 1:3.6 and z is equal to x, a is 1 or 2 and b is 1–3. The most preferable metal silicates are magnesium silicates of the above formula, wherein x is 1, y is 2.6 and z is 1. The metal silicate can be provided in excess and preferably from about 1 to about 50, more preferably from about 5 to about 25, and most preferably from about 10 to about 20 wt. percent of the (hydroxyalkyl amide reaction mixture).

It has been found that the presence of metal silicate reduces the level of alkanolamine in the hydroxyalkyl amide composition to a level that is lower than if the primary and/or secondary alkanolamine, ester and catalyst had not been reacted in the presence of metal silicate compound or alternatively, if the reaction mixture of alkanolamine, ester and catalyst had not been treated with silicate. Before treating the hydroxyalkyl amide composition with metal silicate, it will contain from about 1 to about 6 wt. percent of unreacted alkanolamine. When the hydroxyalkyl amide composition is prepared in the presence of metal silicate or when the hydroxyalkyl amide composition is treated with metal silicate, the amount of unreacted alkanolamine will be reduced to preferably from about 0 to about 0.5 and more preferably from about 0.05 to about 0.2 wt. percent.

The hydroxyalkyl amide which is produced by the reaction of primary and/or secondary alkanolamine and ester can be any amide but preferably a hydroxyalkyl fatty acid amide, more preferably a N,N,-Bis(2-hydroxyethyl) fatty acid amide, and most preferably a N,N-Bis(2-hydroxyethyl) cocoamide.

In addition to reducing the level of primary and/or secondary alkanolamine, the presence of metal silicate can reduce the level of residual catalyst. The level of catalyst can be reduced to a level less than the amount of residual catalyst that would have existed if the primary and/or secondary alkanolamine, ester and catalyst had not been reacted in the presence of the metal silicate compound or had not treated the reaction product of alkanolamine, ester and catalyst with metal silicate. Preferably, the amount of catalyst can be reduced by about 30 wt. percent and more preferably by about 60 wt. percent. The above-described reaction can take place by contacting all of the above-described reactants simultaneously or by a sequential addition of the reactants in any particular order. Preferably, the alkanolamine, ester and catalyst are reacted prior to their exposure to the metal silicate.

The hydroxyalkyl amide composition produced by the method of the invention can be used to provide a decrease in friction in an engine through its use as a fuel or lubricant additive. The fuel or lubricant additive will be part of a liquid engine fuel or lubricant composition comprising a major amount of liquid hydrocarbon fuel or lubricant and a minor amount of a hydroxyalkyl amide obtained from a primary and/or secondary alkanolamine, metal silicate and ester, the hydroxyalkyl amide containing preferably less than about 0.5, more preferably less than about 0.2, and most preferably less than about 0.1 wt. percent alkanolamine. Preferably, it will be added to a liquid engine fuel or lubricant composition in a friction-modifying or lubricity amount. A friction-modifying or lubricity amount will vary greatly depending on its intended use. Preferably, a friction-modifying or lubricity amount will range from about 10 to about 1000, more preferably from about 25 to about 500 and most preferably from about 50 to about 100 ppm. Fuels to which the above-described hydroxyalkyl amide composition can be added include, for example, gasoline, diesel, kerosene, jet fuels, etc., while lubricants can be either synthetic or natural mineral oil based fluids categorized by API as Group I, Group II, Group II, Group IV or Group V base oils or combinations thereof. Various other components can be added to the fuel or lubricant additive composition in addition to the hydroxyalkyl amide composition. These additional components are known to persons skilled in the art and will not be discussed herein.

It will be understood by those skilled in the art that the foregoing hydroxyalkyl amide composition constitutes a complex mixture of compounds including fatty acid amides, as well as fatty acid esters, fatty acid ester-amides, unreacted reactants, free fatty acids, glycerol, and partial fatty acid esters of glycerol (i.e., mono- and di-glycerides). Both primary and secondary hydroxyalkyl fatty acid amides can be produced by the current invention. Preferably, the hydroxyalkyl amide composition produced by this invention will contain from about 10 to about 99, more preferably from about 40 to about 90, and most preferably from about 70 to about 80 wt. percent of hydroxyalkyl amide.

The process of this invention can be carried out over a wide range of temperatures, preferably from about 40° to about 150° C., more preferably from about 50° to about 90° C. and most preferably from about 60° to about 70° C. The duration of the reaction as well can be conducted over a broad range. Preferably, the invention can be carried out for a period of from about 30 minutes to 24 hours, more preferably from about 3 to about 12 hours and most preferably from about 4 to about 8 hours. The reaction can be conducted at any pressure but preferably at reduced pressure. Suitable reduced pressures can range from about 0.5 to about 500 and preferably from about 10 to about 100 torr. The reduced pressure allows for the simultaneous removal of methanol from the reaction medium The hydroxyalkyl amide reaction product of the alkanolamine, ester and catalyst can be reacted with metal silicate under agitation alone and/or in combination with a vacuum of reduced pressures as described above. The resultant product of the hydroxyalkyl amide reaction product and the metal silicate can then be separated by any known process such as filtration, distillation, recrystalization and the like. If the separation is done by filtration, any conventional or known filtration process can be used but preferably the filtration is done through the use of a filtration aid such as Celite 545®, $SiO_2$, diatomaceous earth; diatomite; kieselguhr soda ash flux calcined), and the like The amount of filtration aid will vary greatly but preferably can range from about 0 to about 10, more preferably from about 1 to about 5 and most preferably from about 2 to about 3 wt. percent. The metal silicate will preferably remain in the solid state when mixed with the reaction product of alkanolamine, ester and catalyst. The hydroxyalkyl amide reaction product can pass through the filtration aid along with residual ester. The residual alkanolamine remains with the solid metal silicate.

The reaction vessel used in the process of the invention can be any conventional or known vessel, preferably an agitated vessel and more preferably a stirred tank reactor. The process of the invention can be conducted in batch or in continuous processes.

The following table illustrates the effectiveness of using the above-described metal silicate to remove alkanolamine and sodium as opposed to the presence of alkanolamine and sodium in a hydroxyalkyl amide composition that has not been reacted in the presence of metal silicate. The metal silicate compound that was used was a synthetic magnesium silicate.

TABLE

| | Starting Material | Magnesol ® Treated |
|---|---|---|
| diethanolamine, wt. percent | 1.89 | 0 |
| Sodium, ppm | 2155 | 1027 |

The following example illustrates the current invention.

EXAMPLE

The base N,N-Bis(2-hydroxyethyl) cocoamide was prepared. It used 100 parts of a methyl ester of Industrene® 325 (a coconut oil fatty acid mixture), 45 parts of diethanolamine and 2.3 parts of a 30% concentrate of sodium methoxide in methanol as a catalyst. The materials were mixed under vacuum at 50°–70° C. for approximately 6 hrs resulting in a N,N-Bis(2-hydroxyethyl)cocoamide reaction product mixture with 3.5% residual diethanol amine and 2155 ppm sodium.

Due to the kinetics of this material, the diethanolamine level of the N,N-Bis(2-hydroxyethyl) cocoamide decreased somewhat over time and at the time of testing, the diethanolamine level had decreased to 1.89%. Magnesol® was provided in excess to the reaction product mixture, in that, 5 grams of Magnesol® was added to 25 grams of the reaction product mixture and mixed at room temperature leaving a slurry. This product was then heated to 70° C. under vacuum and kept under constant mixing for one hour. The product was then filtered over Celite® to yield a product with 1027 ppm sodium, but surprisingly 0% diethanolamine.

What is claimed is:

1. A method for reacting at least one primary and/or secondary alkanolamine with at least one ester, optionally, in the presence of catalyst, to provide a reaction mixture containing hydroxyalkyl amide and unreacted alkanolamine, wherein the improvement comprises, carrying out the reaction of an alkanolamine selected from the group consisting of ethanolamine, propanolamine, isopropanolamine, butanolamine, isobutanolamine, methylethanolamine, butylethanolamine, diethanolamine, dipropanolamine, diisopropanolamine, dibutanolamine, diisobutanolamine, and mixtures thereof and ester in the presence of at least one metal silicate or treating the reaction mixture with at least one metal silicate, the metal of the metal silicate being a metal of Group IIA or Group IIIA of the Periodic Table.

2. The method of claim 1 wherein the parent acid of the ester contains from about 4 to about 22 carbon atoms and the parent alkanol of the ester contains from 1 to about 10 carbon atoms.

3. The method of claim 2 wherein the ester is a fatty acid methyl ester or mixture of fatty acid methyl esters.

4. The method of claim 2 wherein the parent acid of the ester is a fatty acid derived from canola oil, castor oil, cocoa butter, coconut oil, cotton seed oil, olive oil, palm kernel oil, palm kernel (olein), palm kernel (stearine), peanut oil, rapeseed oil, safflower oil, soybean oil, sunflower oil, tall oil, corn oil, butter, lard, tallow, yellow grease, blubber, herring, menhaden, sardine oil, babasso oil and mixtures thereof.

5. The method of claim 4 wherein the parent acid of the ester is a fatty acid derived from coconut oil and the parent alkanol of the ester is methanol.

6. The method of claim 2 wherein the parent acid of the ester is selected from the group consisting of butyric, caproic, caprylic, capric, decenoic, lauric, cis-9-dodecenoic, myristic, myristoleic, cis-9-tetradecenoic, pentadecanoic, palmitic, palmitoleic, cis-9-hexadecenoic, heptadecanoic, heptadecenoic, steric, oleic, linoleic, linolenic, ricinoleic, dihydroxystearic, nonadecanoic, arachidic, cis-9, cis-11-eicosenoic, eicosadienoic, eicosatrienoic, arachidonic, eicosapentaenoic, behenic, erucic, docosadienoic, 4,8,12,15, 19-docosapentaenoic, docosahexaenoic, lignoceric, tetracosenoic and mixtures thereof.

7. The method of claim 6 wherein the parent alkanol of the ester is methanol.

8. The method of claim 1 wherein the catalyst is a basic catalyst.

9. The method of claim 8 wherein the basic catalyst is a metal alkoxide or carbonate.

10. The method of claim 9 wherein the metal alkoxide or carbonate is selected from the group consisting of sodium methoxide, sodium ethoxide, sodium propoxide, potassium methoxide, potassium ethoxide, potassium propoxide, potassium carbonate, sodium carbonate, sodium or potassium butoxide, sodium or potassium pentoxide, sodium or potassium hexanoate, sodium carbonate, potassium carbonate, cesium carbonate, calcium carbonate, strontium carbonate, barium carbonate and mixtures thereof.

11. The method of claim 8 wherein the basic catalyst is an organic catalyst selected from the group consisting of tetraalkyl ammonium hydroxide, Ethyl diisopropyl amines, diisopropylethyl amines, 1,8-diazabicyclo[5.4.0] undec-7-ene, 1,5-diazabicyclo[4.3.0] non-5-ene, guanidine and penta methyl guanadine.

12. The method of claim 1 wherein the catalyst is present in an amount of from about 1 to about 100 wt. percent of catalyst concentrate in solvent.

13. The method of claim 12 wherein the catalyst is present in an amount of from about10 to about 50 wt. percent of catalyst concentrate in solvent.

14. The method of claim 13 wherein the catalyst is present in an amount of from about 20 to about 30 wt. percent of catalyst concentrate in solvent.

15. The method of claim 10 wherein the metal alkoxide or carbonate catalyst is present in an amount of from about 0.05 to about 1.00 wt. percent.

16. The method of claim 15 wherein the metal alkoxide or carbonate catalyst is present in an amount of from about 0.25 to about 0.75 wt. percent.

17. The method of claim 16 wherein the metal alkoxide or carbonate catalyst is present in an amount of from about 0.40 to about 0.60 wt. percent.

18. The method of claim 11 wherein the organic catalyst is present in an amount of from about 0.05 to about 1.00 wt. percent.

19. The method of claim 18 wherein the organic catalyst is present in an amount of from about 0.25 to about 0.75 wt. percent.

20. The method of claim 19 wherein the organic catalyst is present in an amount of from about 0.40 to about 0.60 wt. percent.

21. The method of claim 1 wherein the metal silicate is of the general formula $xM_aO_b:ySiO_2:zH_2O$ wherein M is any metal of Group IA, Group IIA or Group IIIA of The Periodic Table, x and y are in a molar ratio of from about 1.5:1 to about 1:3.6 and z is equal to x, a is 1 or 2 and b is 1–3.

22. The method of claim 21 wherein in the formula of the metal silicate, x is 1, y is 2.6 and z is 1.

23. The method of claim 21 wherein the metal in the metal silicate is magnesium, calcium, aluminum, sodium.

24. The method of claim 22 wherein the metal in the metal silicate is magnesium, calcium, aluminum, sodium.

25. The method of claim 21 wherein the metal silicate is present at a level of from about 1 to about 50 wt. percent of hydroxyalkyl amide reaction mixture.

26. The method of claim 21 wherein the metal silicate is present at a level of from about 10 to about 20 wt. percent of hydroxyalkyl amide reaction mixture.

27. The method of claim 22 wherein the metal silicate is present at a level of from about 1 to about 50 wt. percent of hydroxyalkyl amide reaction mixture.

28. The method of claim 22 wherein the metal silicate is present at a level of from about 10 to about 20 wt. percent of hydroxyalkyl amide reaction mixture.

29. The method of claim 1 wherein the reaction mixture treated with the metal silicate contains from about 0 to about 0.5 wt. percent unreacted alkanolamine.

30. The method of claim 1 wherein the reaction mixture treated with the metal silicate contains from about 0.05 to about 0.2 wt. percent unreacted alkanolamine.

31. The method of claim 1 wherein the reaction of alkanolamine and ester is carried out in the presence of catalyst and treated with metal silicate with the amount of catalyst being reduced by about 30 percent.

32. The method of claim 1 wherein the reaction of alkanolamine and ester is carried out in the presence of catalyst and treated with metal silicate with the amount of catalyst being reduced by about 60 percent.

33. A method for making a hydroxyalkyl amide which comprises reacting at least one primary and/or secondary alkanolamine with at least one ester, optionally, in the presence of catalyst, to provide a reaction mixture containing hydroxyalkyl amide and unreacted alkanolamine, the reaction of alkanolamine and ester being carried out in the presence of at least one metal silicate or the reaction mixture being treated with at least one metal silicate, the metal of the metal silicate being a metal of Group IA, Group IIA or Group IIIA of the Periodic Table.

34. The method of claim 33 wherein the primary and/or secondary alkanolamine is of the general formula RNHR' wherein R is hydroxyalkyl of from about 2 to about 10 carbon atoms, hydroxyalkylether and/or combinations thereof, and R' is hydrogen, alkyl of from 1 to about 10 carbon atoms, hydroxyalkylether and/or combinations thereof or hydroxyalkyl of from 2 to about 10 carbon atoms, hydroxyalkylether and/or combinations thereof.

35. The method of claim 33 wherein the alkanolamine is selected from the group consisting of ethanolamine, propanolamine, isopropanolamine, butanolamine, isobutanolamine, methylethanolamine, butylethanolamine, diethanolamine, dipropanolamine, diisopropanolamine, dibutanolamine, diisobutanolamine, and mixtures thereof.

36. The method of claim 33 wherein the parent acid of the ester contains from about 4 to about 22 carbon atoms and the parent alkanol of the ester contains from 1 to about 10 carbon atoms.

37. The method of claim 36 wherein the ester is a fatty acid methyl ester or mixture of fatty acid methyl esters.

38. The method of claim 33 wherein the parent acid of the ester is a fatty acid derived from canola oil, castor oil, cocoa butter, coconut oil, cotton seed oil, olive oil, palm kernel oil, palm kernel (olein), palm kernel (stearine), peanut oil, rapeseed oil, safflower oil, soybean oil, sunflower oil, tall oil fatty acid, corn oil, butter, lard, tallow, yellow grease, blubber, herring, menhaden, sardine, babasso and mixtures thereof.

39. The method of claim 38 wherein the parent acid of the ester is a fatty acid derived from coconut oil and the parent alkanol of the ester is methanol.

40. The method of claim 36 wherein the parent acid of the ester is selected from the group consisting of butyric, caproic, caprylic, capric, decenoic, lauric, cis-9-dodecenoic, myristic, myristoleic, cis-9-tetradecenoic, pentadecanoic, palmitic, palmitoleic, cis-9-hexadecenoic, heptadecanoic, heptadecenoic, steric, oleic, linoleic, linolenic, ricinoleic, dihydroxystearic, nonadecanoic, arachidic, cis-9, cis-11-eicosenoic, eicosadienoic, eicosatrienoic, arachidonic, eicosapentaenoic, behenic, erucic, docosadienoic, 4,8,12,15, 19-docosapentaenoic, docosahexaenoic, lignoceric, tetracosenoic and mixtures thereof.

41. The method of claim 40 wherein the parent alkanol of the ester is methanol.

42. The method of claim 36 wherein the catalyst is a basic catalyst.

43. The method of claim 42 wherein the basic catalyst is a metal alkoxide or carbonate.

44. The method of claim 43 wherein the metal alkoxide or carbonate is selected from the group consisting of sodium methoxide, sodium ethoxide, sodium propoxide, potassium methoxide, potassium ethoxide, potassium propoxide, potassium carbonate, sodium carbonate, sodium or potassium butoxide, sodium or potassium pentoxide, sodium or potassium hexanoate, sodium carbonate, potassium carbonate, cesium carbonate, calcium carbonate, strontium carbonate, barium carbonate and mixtures thereof.

45. The method of claim 42 wherein the basic catalyst is an organic catalyst selected from the group consisting of tetraalkyl ammonium hydroxide, Ethyl di-isopropyl amines, diisopropyl ethyl amines, 1,8-diazabicyclo[5.4.0] undec-7-ene, 1,5-diazabicyclo[4.3.0] non-5-ene, guanidine, penta methyl guanadine.

46. The method of claim 33 wherein the catalyst is present in an amount of from about 1 to about 100 wt. percent of catalyst concentrate in solvent.

47. The method of claim 46 wherein the catalyst is present in an amount of from about 10 to about 50 wt. percent of catalyst concentrate in solvent.

48. The method of claim 47 wherein the catalyst is present in an amount of from about 20 to about 30 wt. percent of catalyst concentrate in solvent.

49. The method of claim 44 wherein the metal alkoxide or carbonate catalyst is present in an amount of from about 0.05 to about 1.00 wt. percent.

50. The method of claim 49 wherein the metal alkoxide or carbonate catalyst is present in an amount of from about 0.25 to about 0.75 wt. percent.

51. The method of claim 50 wherein the metal alkoxide or carbonate catalyst is present in an amount of from about 0.40 to about 0.60 wt. percent.

52. The method of claim 45 wherein the organic catalyst is present in an amount of from about 0.05 to about 1.00 wt. percent.

53. The method of claim 52 wherein the organic catalyst is present in an amount of from about 0.25 to about 0.75 wt. percent.

54. The method of claim 53 wherein the organic catalyst is present in an amount of from about 0.40 to about 0.60 wt. percent.

55. The method of claim 33 wherein the metal silicate is of the general formula $xM_aO_b:ySiO_2:zH_2O$ wherein M is any metal of Group IA, Group IIA or Group IIIA of The Periodic Table, x and y are in a molar ratio of from about 1.5:1 to about 1:3.6 and z is equal to x, a is 1 or 2 and b is 1–3.

56. The method of claim 55 wherein in the formula of the metal silicate x is 1, y is 2.6 and z is 1.

57. The method of claim 55 wherein the metal in the metal silicate is magnesium, calcium, aluminum, sodium.

58. The method of claim 56 wherein the metal in the metal silicate is magnesium.

59. The method of claim 55 wherein the metal silicate is present at a level of from about 1 to about 50 wt. percent of hydroxyalkyl amide reaction mixture.

60. The method of claim 55 wherein the metal silicate is present at a level of from about 10 to about 20 wt. percent of hydroxyalkyl amide reaction mixture.

61. The method of claim 56 wherein the metal silicate is present at a level of from about 1 to about 50 wt. percent of hydroxyalkyl amide reaction mixture.

62. The method of claim 56 wherein the metal silicate is present at a level of from about 10 to about 20 wt. percent of hydroxyalkyl amide reaction mixture.

63. The method of claim 33 wherein the hydroxyalkyl amide contains not more than about 0.5 wt. percent unreacted alkanolamine.

64. The method of claim 33 wherein the reaction of alkanolamine and ester is carried out in the presence of catalyst and treated with metal silicate with the amount of catalyst being reduced by about 30 wt. percent.

65. The method of claim 33 wherein the reaction of alkanolamine and ester is carried out in the presence of catalyst and treated with metal silicate with the amount of catalyst being reduced by about 60 wt. percent.

* * * * *

UNITED STATES PATENT AND TRADEMARK OFFICE
CERTIFICATE OF CORRECTION

PATENT NO.       : 7,244,857 B2
APPLICATION NO.  : 10/713805
DATED            : July 17, 2007
INVENTOR(S)      : Fox et al.

It is certified that error appears in the above-identified patent and that said Letters Patent is hereby corrected as shown below:

At column 8, line 3 of claim 21, please delete "HA" and insert

--IIA-- in its place.

Signed and Sealed this

Twenty-third Day of October, 2007

JON W. DUDAS
*Director of the United States Patent and Trademark Office*